United States Patent

Rufer et al.

[11] B 3,992,374
[45] Nov. 16, 1976

[54] AMINO-SUBSTITUTED NITROIMIDAZOLYL-METHYLENEAMINOIMIDAZOLIDINONES

[75] Inventors: Clemens Rufer; Hans-Joachim Kessler, both of Berlin, Germany

[73] Assignee: Schering Aktiengesellschaft, Berlin & Bergkamen, Germany

[22] Filed: June 28, 1974

[21] Appl. No.: 484,067

[44] Published under the second Trial Voluntary Protest Program on February 17, 1976 as document No. B 484,067.

[30] Foreign Application Priority Data

July 7, 1973   Germany............................ 2335144

[52] U.S. Cl.......................... 260/240 A; 260/240 G; 260/240.1; 260/309; 260/309.7; 424/273
[51] Int. Cl.².............. C07D 401/12; C07D 401/14
[58] Field of Search.......... 260/240 A, 240 G, 240.1

[56] References Cited
UNITED STATES PATENTS 3,752,809   8/1973   Rufer et al...................... 260/240 A
3,832,352   8/1974   Ilvespää............................. 423/273

OTHER PUBLICATIONS

Snyder et al., J. Med. Chem. 13 (1970), No. 4, pp. 756–759.

*Primary Examiner*—Arthur P. Demers
*Attorney, Agent, or Firm*—Millen, Raptes & White

[57] ABSTRACT

Amino-substituted nitroimidazolyl-methyleneaminoimidazolidinones of the formula

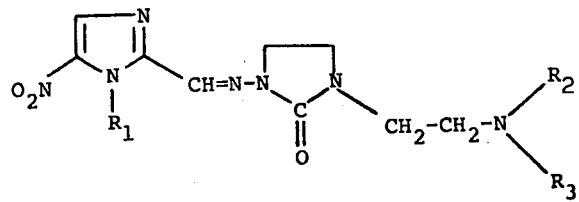

wherein —$NR_2R_3$ is dialkylamino or heterocyclic amino, and the physiologically acceptable salts thereof, possess antitrichomonial activity.

8 Claims, No Drawings

AMINO-SUBSTITUTED NITROIMIDAZOLYL-METHYLENEAMINOIMIDAZOLIDINONES

BACKGROUND OF THE INVENTION

This invention relates to novel amino-substituted nitroimidazolyl-methyleneaminoimidazolidinones.

The effectiveness of nitroimidazoles against trichomonads has been known since the discovery of the antibiotic azomycin (2-nitroimidazole, S. Nakamura and H. Umezawa, J. Antibiotics [Tokyo], 9A, 66 [1955]). These and other 2-nitroimidazoles, however, have proved to be no better, in vitro, than metronidazole (see below) (G. C. Lancini, E. Lazzari, R. Pallanea, Il Farmaco Ed. Sc. 21, 278 [1966]), and the $CD_{50}$- and $LD_{50}$-values were considerably more unfavorable (E. Grunberg, E. Titsworth, Antimicrobial Agents and Chemotherapy 1965, 1966, 478). Only the 5-nitroimidazoles have, from a large number of synthesized compounds (C. Cosar, "Arzneimittelforschung" [Drug Research] 16, 23 [1966]), yielded an anti-trichomonial compound which is significantly effective in vivo, viz., metronidazole (5-nitro-2-methyl-1-(2-hydroxyethyl)-imidazole; see also French Patent No. 1,212,028), with a minimum inhibitory concentration of 2.5 μg./ml. against Trichomonas vaginalis.

It has now been found that the condensation products of 1-alkyl-5-nitro-2-imidazolylcarboxaldehydes with 1-amino-2-imidazolidinones substituted in the 3-position with tert.-aminoethyl have approximately the same effective strength against Trichomonas vaginalis in the plate dilution test as metronidazole. Moreover, in contrast to metronidazole, marked blood levels become apparent after oral administration of the novel compounds. Thus, the novel compounds are also excellently suitable for the treatment of infections localized in the tissue.

SUMMARY OF THE INVENTION

In a composition aspect, this invention relates to amino-substituted nitroimidazole methyleneaminoimidazolidinones of the general Formula I

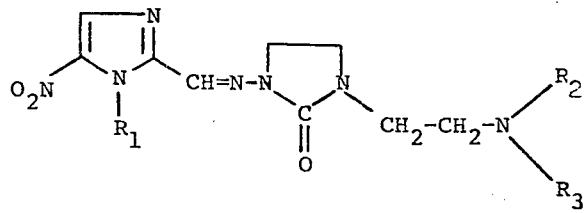

wherein $R_1$ is alkyl of 1-4 carbon atoms, inclusive, and $R_2$ and $R_3$, which can be alike or different, each are alkyl of 1-4 carbon atoms, inclusive, or $R_2$ and $R_3$, collectively with the N-atom, are a heterocyclic amino group, and physiologically acceptable acid addition salts thereof.

In another composition aspect, this invention relates to pharmaceutical compositions comprising a compound of Formula I in admixture with a pharmaceutically acceptable carrier.

DETAILED DISCUSSION

In Formula I, $R_2$ and $R_3$ collectively with the amino nitrogen atom can be dialkylamino, e.g., dimethylamino, diethylamino, methyl, ethylamino, di-n-propylamino, methyl, n-butylamino, or heterocyclicamino of 5- or 6-ring members and 1-2 hetero ring atoms, i.e., they form a 5- or 6-membered ring, optionally substituted by alkyl of 1-4 carbon atoms, and optionally containing an additional N-, O- or S-atom as a ring member, e.g., pyrrolidino, 2-methyl-pyrrolidino, 2,5-dimethylpyrrolidino, piperidino, 4-methylpiperidino, morpholino, thiomorpholino, imidazolino, isoimidazolino, indolino, piperazino, N'-lower-alkylpiperazino Preferred compounds of Formula I are those wherein
a. $R_1$ is $CH_3$;
b. $R_2$ and $R_3$ together with the N-atom preferably are dialkylamino wherein each alkyl is of 1 to 4 carbon atoms, inclusive, pyrrolidino, piperidino, morpholino or N'-methylpiperazino, especially those of (a);
c. they are in the form of a pharmaceutically acceptable acid addition salt, especially those of (a) and (b).

Examples of physiologically acceptable acid addition salts are those of inorganic acids, e.g., hydrochloric acid, sulfuric acid, phosphoric acid, and of organic acids, e.g., acetic acid, propionic acid, lactic acid, citric acid, benzoic acid, succinic acid and heptagluconic acid.

The novel compounds can be prepared by reacting an aldehyde of the general Formula II

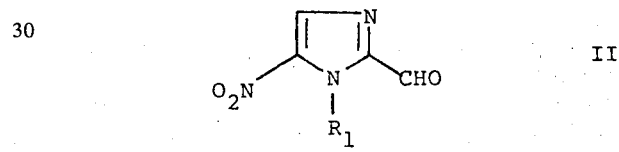

wherein $R_1$ has the values given above, with a 1-amino-2-imidazolidinone of the general Formula III

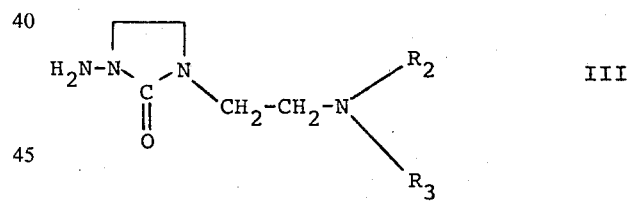

wherein $R_2$ and $R_3$ have the values given above, or with a reactive functional derivative of the 3-amino group.

Suitable reactive derivatives of the amino group are derivatives with carbonyl compounds, e.g., benzylideneamino compounds. Such compounds of general Formula III are described in the Journal of Medicinal Chemistry 1970, Vol. 13, pp. 756–759.

The reaction of compounds II with compounds III takes place ordinarily at room temperature or at elevated temperature up to the boiling point, in an acidic medium, preferably in aqueous and/or alcoholic hydrochloric acid. Depending on the reaction temperature, the reaction is complete after 15 minutes to 48 hours.

The novel compounds possess good antimicrobial effects, especially against protozoa and, among these, specifically against Trichomonas vaginalis, as will be demonstrated by the following example of 1-(2-morpholinoethyl)-3-(1-methyl-5-nitro-2-imidazolyl-methyleneamino)-2-imidazolidinone (A) as compared to metronidazole.

| Compound | Min. Inh. Conc. in μg./ml. against Trich. vaginalis | Oral Activity 100 mg.kg. in Mice | |
|---|---|---|---|
| | | Urine | Blood |
| A | 1.6 | — | — |
| Metronidazole | 1.6 | — | — |

With equally good effectiveness in the plate dilution test against Trichomonas vaginalis, the novel compounds show marked blood levels after oral administration of 100 mg. of effective agent per kg. of mouse.

The novel compounds are useful for the treatment of trichomoniasis, especially Trichomonas vaginalis infections. They can be employed in substantially the same manner as the known compound metronidazole. For such use, they can be formulated into conventional drug forms with the additives, carrier substances, and flavoring agents customary in pharmaceutical preparations which do not deleteriously react with the effective agents, employing conventional methods. For oral application, particularly suitable are tablets, dragees, capsules, pills, suspensions and solutions. Such compositions can employ, for example, water, alcohol, polyethylene glycols, gelatin, sucrose, lactose, amylose in solutions and suspensions and, e.g., magnesium stearate, talc, lactose, amylose, in tablets. The concentration of the effective agent in the thus-formulated compositions is dependent on the activity of the specific compound employed, the responsiveness of the individual patient and the mode of administration. Generally, they contain about 0.05 to 2.0 g., preferably about 0.1 to 0.5 g. of a compound of this invention and 0.1 to 5 g. of a pharmaceutical carrier per unit dose.

For topical application, the compounds of this invention can be applied as a powder, solution, suspension, foam or aerosol or as vaginal tablets and suppositories. For parenteral application, aqueous or oily solutions or suspensions can be used.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

1-(2-Morpholinoethyl)-3-(1-methyl-5-nitro-2-imidazolylmethyleneamino)-2-imidazolidinone, Monohydrate 0.9 g. of 1-benzylideneamino-3-(2-morpholinoethyl)-2-imidazolidinone and 0.46 g. of 1-methyl-5-nitro-2-imidazolylcarboxaldehyde are heated for 30 minutes to 100° C. in 10 ml. of 1N hydrochloric acid. After cooling, the mixture is made alkaline with 1N sodium hydroxide solution, and the product is vacuum-filtered, thus obtaining 0.9 g. (85% of theory) of the title compound, m.p. 173° C.

EXAMPLE 2

1-(2-Diethylaminoethyl)-3-(1-methyl-5-nitro-2-imidazolyl-methyleneamino)-2-imidazolidinone The title compound is produced analogously to Example 1 from 1-benzylideneamino-3-(2-diethylaminomethyl)-2-imidazolidinone and 1-methyl-5-nitro-2-imidazolylcarboxaldehyde. Yield: 58%, m.p. 178° C.

EXAMPLE 3

1-(2-Pyrrolidinoethyl)-3-(1-methyl-5-nitro-2-imidazolylmethyleneamino)-2-imidazolidinone The title compound is produced analogously to Example 1 from 1-benzylideneamino-3-(2-pyrrolidinoethyl)-2-imidazolidinone and 1-methyl-5-nitro-2-imidazolylcarboxaldehyde. Yield 55%, m.p. 187° C.

Following the procedures of Examples 1-3, 1-(2-piperidinoethyl)-3-(1-methyl-5-nitro-2-imidazolyl-methylene-amino)-2-imidazolidino and 1-(2-N'-methylpiperazinoethyl)-3-(1-methyl-5-nitro-2-imidazolylmethyleneamino)-2-imidazolidino are produced from 1-benzylideneamino-3-(2-piperidinoethyl)-2-imidazolidinone and 1-benzylideneamino-3-(2-N'-methylpiperazinoethyl)-2-imidazolidinone, respectively, as solutions of their hydrochloride addition salts which can be isolated as such or converted as in Example 1 to their free base form with 1N sodium hydroxide.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An amino-substituted nitroimidazolylmethyleneamino-imidazolidinone of the formula

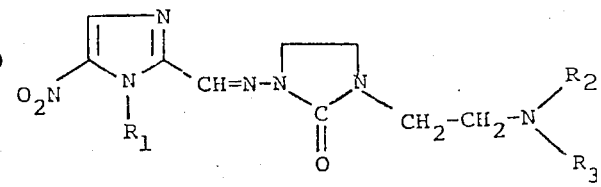

wherein $R_1$ is alkyl of 1–4 carbon atoms and $-NR_2R_3$ is dialkylamino wherein alkyl is of 1 to 4 carbon atoms, pyrrolidino, piperidino, morpholino or N-methylpiperazino, or a physiologically acceptable acid addition thereof.

2. A compound of claim 1 wherein $R_1$ is methyl.

3. A compound of claim 1 wherein $-NR_2R_3$ is diethylamino.

4. A compound of claim 1 wherein $-NR_2R_3$ is pyrrolidino.

5. A compound of claim 1 wherein $-NR_2R_3$ is morpholino.

6. A compound of claim 1, 1-(2-morpholinoethyl)-3-(1-methyl-5-nitro-2-imidazolylmethyleneamino)-2-imidazolidinone, monohydrate.

7. A compound of claim 1, 1-(2-diethylaminoethyl)-3-(1-methyl-5-nitro-2-imidazolylmethyleneamino)-2-imidazolidinone.

8. A compound of claim 1, 1-(2-pyrrolidinoethyl)-3-(1-methyl-5-nitro-2-imidazolylmethyleneamino-2-imidazolidinone.

* * * * *